(12) United States Patent
Tanaka

(10) Patent No.: US 6,333,022 B1
(45) Date of Patent: Dec. 25, 2001

(54) PESTICIDAL COMPOSITION

(75) Inventor: Yasuyori Tanaka, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/536,155

(22) Filed: Mar. 28, 2000

(30) Foreign Application Priority Data

Apr. 28, 1999 (JP) .................................................. 11-121952

(51) Int. Cl.7 ...................................................... A01N 25/06
(52) U.S. Cl. .............................. 424/45; 424/405; 514/535
(58) Field of Search ............................ 514/535; 424/405, 424/406, 45

(56) References Cited

U.S. PATENT DOCUMENTS 5,698,591 * 12/1997 Mori et al. ............................ 514/535
6,037,371 * 3/2000 Kawada ................................ 514/535

FOREIGN PATENT DOCUMENTS

| 0 778 268 A1 | 6/1997 | (EP) . |
| 0 909 531 A1 | 4/1999 | (EP) . |
| 57-156407 | 9/1982 | (JP) . |
| 8-319202 | 12/1996 | (JP) . |
| 11-100304 | 4/1999 | (JP) . |

* cited by examiner

Primary Examiner—Neil S. Levy
(74) Attorney, Agent, or Firm—Sughrue Mion, PLLC

(57) ABSTRACT

A pesticidal liquid composition which comprises 0.01 to 5% by weight of 2-methoxycarbonyl-4-chlorotrifluoromethanesulfonanilide and 35 to 99.9% by weight of a saturated hydrocarbon having 13 to 17 of carbon number or an aerosol composition which comprises said liquid composition and a propellant shows an excellent pesticidal effect.

3 Claims, No Drawings

PESTICIDAL COMPOSITION

FIELD OF THE INVENTION

The present invention relates to pesticidal liquid compositions and pesticidal aerosol compositions.

BACKGROUND ART

It is known that 2-methoxycarbonyl-4-chlorotrifluoromethane-sulfonanilide can be used as an active ingredient of an insecticidal/acaricidal composition in Japanese Laid-open Patent Nos. sho-57-156407A and hei-8-319202A. However, its insecticidal/acaricidal effect may be insufficient when used as a formulation such as oil solution, aerosol and the like.

SUMMARY OF THE INVENTION

The present invention provides a composition comprising 2-methoxycarbonyl-4-chlorotrifluoromethanesulfonanilide of the formula:

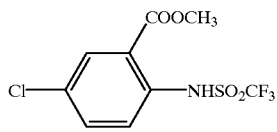

and a saturated hydrocarbon having a specific carbon number which has an extremely good pesticidal activity and especially shows an excellent effect in a formulation of a pesticidal aerosol composition.

The pesticidal composition of the present invention comprises 2-methoxycarbonyl-4-chlorotrifluoromethanesulfonanilide (hereinafter referred to as Compound A) and a saturated hydrocarbon having 13 to 17 of carbon number. The pesticidal composition of the present invention can be a liquid composition which comprises 0.01 to 5% by weight of Compound A and 40 to 99.9% by weight of a saturated hydrocarbon(s) having 13 to 17 of carbon number. In other words, the pesticidal liquid composition of the present invention comprises Compound A and at least one saturated hydrocarbon having 13 to 17 of carbon number wherein the amount of Compound A is 0.01 to 5% by weight and the total amount of said saturated hydrocarbons is 35 to 99.9% by weight therein. Further, the pesticidal composition of the present invention can be an aerosol composition which comprises the above liquid composition and a propellant.

DETAILED DESCRIPTION OF THE INVENTION

In the present invention, the saturated hydrocarbons having 13 to 17 of carbon number may be branched saturated hydrocarbons, normal chained saturated hydrocarbons (tridecane, tetradecane, pentadecane, hexadecane and heptadecane), alicyclic saturated hydrocarbons and mixtures thereof.

Typical examples of said saturated hydrocarbon include petroleum solvent in the market such as Isopar M, Isopar V (mixtures of branched saturated hydrocarbons and alicyclic hydrocarbons produced by Exxon Chemical), Norpar 13, Norpar 15 (normal chained saturated hydrocarbons produced by Exxon Chemical), Neo-chiosol (normal chained saturated hydrocarbons produced by Chuo Kasei Co., Ltd.) and Exxol D110 (mixtures of normal chained and branched saturated hydrocarbons and alicyclic hydrocarbons produced by Exxon Chemical), and mixtures thereof.

The weight ratio of Compound A and the saturated hydrocarbon in the pesticidal composition of the present invention is usually from 1:15 to 1:9999, preferably 1:20 to 1:200.

The pesticidal composition of the present invention optionally comprises one or more of the other pesticidal active ingredients, synergists, perfumes and auxiliary solvents. Examples of the other pesticidal active ingredient include allethrin, tetramethrin, prallethrin, phenothrin, resmethrin, cyphenothrin, permethrin, cypermethrin, deltamethrin, cyfluthrin, furamethrin, imiprothrin, etofenprox, fenitrothion, propoxur, metoxadiazon, pyriproxyfen, methoprene, hydroprene, diflubenzuron, cyromazin, phenyl salicylate, benzyl benzoate, diethyl tetrephthalate and their pesticidally active optical/geometrical isomers if any. Examples of the synergist include piperonylbutoxide, N-(2-ethylhexyl)bicyclo[2.2.1]hept-5-ene-2,3-dicarboxyimide, octachlorodipropyl ether.

Examples of the auxiliary solvent include alkylbenzenes such as trimethylbenzene and dodecylbenzene; diarylethanes such as phenylxylylethane; ketones such as acetone, methyl ethyl ketone, methyl isobutyl ketone, cyclohexanone and isophorone; alcohols such as methanol, ethanol, isopropyl alcohol, hexanol and benzyl alcohol; mono- or diethers of ethylene glycol and propylene glycol; diethylene glycol monomethyl ether and monoethyl ether; 3-methoxy-3-methyl-1-butanol; 3-methoxy-3-methyl-1-butyl acetate; N-methyl-2-pyrrolidone; and propylene carbonate.

The aerosol composition of the present invention preferably utilized for total release type aerosol. Said aerosol composition usually comprises 20 to 50% by weight of the liquid composition of the present invention and 50 to 80% by weight of a propellant. Examples of the propellant include propane, n-butane, isobutane, dimethyl ether and mixtures thereof.

The liquid composition of the present invention, for example, can be prepared by mixing and dissolving Compound A and the saturated hydrocarbon having 13 to 17 of carbon number, and optionally the other pesticidal active ingredient mentioned above, synergist, perfume and auxiliary solvent, under room temperature or with heating.

Further, the aerosol composition of the present invention, for example, can be prepared by charging the liquid composition of the present invention in an aerosol container, fitting an aerosol valve to the container and charging a propellant through the stem.

In the case that the liquid composition of the present invention is used for pest-control, the liquid composition, which is usually a pesticidal oil solution, may be applied as it is.

In addition, the total release aerosol formulations of the present invention are more effective for controlling pests such as insects and acarina hiding in a space or shelter indoors. A total release aerosol is a known formulation that can release all the contents containing a pesticidal active ingredient in the aerosol container in a short time, and is usually used in a closed room. The total release aerosol comprises the liquid composition of the present invention and a propellant in an aerosol container crimped an aerosol valve and fitted total release type actuator on.

Example of the pests controlled by the present composition include acarina and insects. They are exemplified by house dust mites (for example, Dermatophagoides spp. such as *Dermatophagoides farinae, Dermatophagoides pteronyssinus* and so on; Acaridae such as *Lardoglyphus konoi, Tyrophagus putrescentiae, Aleuroglyphus ovatus* and so on;

Glycyphagidae such as *Glycyphagus privatus*, *Glycyphagus domesticus*, *Glycyphagus destructor* and so on; Cheyletidae such as *Chelacaropsis moorei*, *Chelacaropsis malaccensis*, *Cheyletus fortis*, *Cheyletus eruditus*, *Chelatomorpha lepidopterorum* and so on; Macronyssidae such as *Ornithonyssus hacoti*, *Ornithonyssus sylviarum*, *Dermanyssus gallinae*, *Dermanyssus hirundinis* and so on; Haplochthonius spp.; Pyemotidae; itch mites; and so on); fleas such as cat flea, dog flea and so on; cockroaches such as German cockroach, smokeybrown cockroach, American cockroach and so on; Psocoptera such as *Liposcelis bostrychophilus*, *Liposcelis entomophilus* and so on; Formicidae such as *Monomorium pharaonis* and so on; Cimicidae such as *Cimex lectularius* and so on. Especially, the present composition is very effective for controlling house dust mites.

EXAMPLES

The present invention will be explained in detail by examples below, but the present invention is not limited to these examples.

Formulation Example 1

In an aerosol container, 0.33 part by weight of Compound A was charged and Isopar M (hydrocarbon solvent produced by Exxon Chemical, containing about 75% by volume of $C_{13-17}$ branched saturated hydrocarbons therein) was added thereto to make the total 50 parts by weight. An aerosol valve (two stem orifices of 0.51 mm in diameter, housing main orifice of 2.03 mm in diameter, vapor tap orifice of 0.51 mm in diameter, manufactured by Precision Valve Japan LTD) was crimped to the aerosol container, to which 50 parts by weight of liquefied petroleum gas (commercial name: Deodorized LPG4.8KG, 4.8 kg/cm² in gauge pressure at 20° C., produced by Daido-Hokusan) were charged and an actuator for total release aerosol (total release type actuator, 0.41 mm in terminal orifice diameter, manufactured by Precision Valve Japan LTD) was fitted to give Aerosol 1 having 25 g of the aerosol composition of the present invention.

Formulation Example 2

In an aerosol container, 0.33 part by weight of Compound A and 25 parts by weight of isopropyl alcohol (produced by Kanto Chemical Co., INC.) were charged and Isopar M was added thereto to make the total 50 parts by weight. An aerosol valve (two stem orifices of 0.51 mm in diameter, housing main orifice of 2.03 mm in diameter, vapor tap orifice of 0.51 mm in diameter, manufactured by Precision Valve Japan LTD) was crimped to the aerosol container, to which 50 parts by weight of liquefied petroleum gas (commercial name : Deodorized LPG4.8KG, 4.8 kg/cm² in gauge pressure at 20° C., produced by Daido-Hokusan) were charged and an actuator for total release aerosol (0.41 mm in terminal orifice manufactured by Precision Valve Japan LTD) was fitted to give Aerosol 2 having 25g of the aerosol composition of the present invention.

Formulation Example 3

In an aerosol container, 0.33 part by weight of Compound A was charged and Isopar M was added thereto to make the total 25 parts by weight. An aerosol valve (two stem orifices of 0.51 mm in diameter, housing main orifice of 2.03 mm in hole diameter, vapor tap orifice of 0.51 mm in diameter, manufactured by Precision Valve Japan LTD) was crimped to the aerosol container, to which 75 parts by weight of dimethyl ether (produced by Daido-Hokusan) were charged and an actuator for total release aerosol (0.41 mm in terminal orifice diameter, manufactured by Precision Valve Japan LTD) was fitted to give Aerosol 3 having 25 g of the aerosol composition of the present invention.

Formulation Example 4

In an aerosol container, 0.41 part by weight of Compound A was charged and Isopar V (hydrocarbon solvent produced by Exxon Chemical, containing about 68% by volume of $C_{13-17}$ branched saturated hydrocarbons therein) was added thereto to make the total 25 parts by weight. An aerosol valve (two stem orifices of 0.51 mm in diameter, housing main orifice of 2.03 mm in diameter, vapor tap orifice of 0.51 mm in diameter, produced by Precision Valve Japan LTD) was crimped to the aerosol container, to which 75 parts by weight of dimethyl ether (produced by Daido-Hokusan) were charged and an actuator for total release aerosol (0.41 mm in terminal orifice diameter, manufactured by Precision Valve Japan LTD) was fitted to give Aerosol 4 having 20 g of the aerosol composition of the present invention.

Formulation Example 5

In an aerosol container, a mixture of 0.5 part by weight of Compound A, 1.5 parts by weight of d-phenothrin and 2.5 parts by weight of ethanol blended with heating, is charged and Isopar M is added thereto to make the total 25 parts by weight. An aerosol valve (two stem orifices of 0.51 mm in diameter, housing main orifice of 2.03 mm in diameter, vapor tap orifice of 0.51 mm in diameter, manufactured by Precision Valve Japan LTD) is crimped to the aerosol container, to which 75 parts by weight of dimethyl ether (produced by Daido-Hokusan) are charged and an actuator for total release aerosol (total release type actuator, 0.41 mm in terminal orifice diameter, manufactured by Precision Valve Japan LTD) is fitted to give Aerosol 5 having 25 g of the aerosol composition of the present invention.

Formulation Example 6

The same procedure as Formulation Example 5, except 1.5 parts by weight of piperonylbutoxide and 1.0 part by weight of isopropyl alcohol are used in place of 1.5 parts by weight of d-phenothrin and 2.5 parts by weight of ethanol, is carried out to give Aerosol 6 having 25 g of the aerosol composition of the present invention.

Formulation Example 7

The same procedure as Formulation Example 5, except 0.2 part by weight of metoxadiazon, 1.3 parts by weight of d-phenothrin, 1.5 parts by weight of piperonylbutoxide and 0.5 part by weight of propylene glycol monomethyl ether are used in place of 1.5 parts by weight of d-phenothrin and 2.5 parts by weight of ethanol, is carried out to give Aerosol 7 having 25 g of the aerosol composition of the present invention.

Formulation Example 8

The same procedure as Formulation Example 5, except 0.25 part by weight of Compound A, 1.25 parts by weight of metoxadiazon, 0.5 part by weight of d-phenothrin, 1.5 parts by weight of N-(2-ethylhexyl)bicyclo[2.2.1]hept-5-ene-2,3-dicarboxyimide and 2.5 parts by weight of diethylene glycol monoethyl ether are used in place of 0.5 part by weight of Compound A, 1.5 parts by weight of d-phenothrin and 2.5 parts by weight of ethanol, is carried out to give Aerosol 8 having 25 g of the aerosol composition of the present invention.

Reference Formulation Example 1

The same procedure as Formulation Example 1, except using Isopar E (hydrocarbon solvent produced by Exxon Chemical, mainly $C_{7-9}$ branched saturated hydrocarbons) in place of Isopar M, was performed to give Reference Aerosol 1.

Reference Formulation Example 2

The same procedure as Formulation Example 4, except using Isopar G (hydrocarbon solvent produced by Exxon Chemical, mainly $C_{9-12}$ branched saturated hydrocarbons) in place of Isopar V, was performed to give Reference Aerosol 2.

Reference Formulation Example 3

The same procedure as Formulation Example 4, except using Isopar H (hydrocarbon solvent produced by Exxon Chemical, mainly $C_{11-12}$ branched saturated hydrocarbons) in place of Isopar V, was performed to give Reference Aerosol 3.

Reference Formulation Example 4

The same procedure as Formulation Example 4, except using Isopar L (hydrocarbon solvent produced by Exxon Chemical, mainly $C_{11-12}$ branched saturated hydrocarbons, and containing about 20% by volume of $C_{13-17}$ branched saturated hydrocarbons therein) in place of Isopar V, was performed to give Reference Aerosol Formulation 4.

Test Example

Filter paper having 4 cm in diameter was put on an aluminum plate and the filter paper was surrounded by adhesives for preventing from running away of house dust mites. And then, twenty to fifty mites (*Tyrophagus putrescentiae*) were released on the filter paper.

At three corners of the bottom of a 1.8 m cubed chamber, three aluminum plates above were put at intervals of 30 cm from the corners. On the other hand, the aerosol formulation of the present invention or the reference aerosol formulation was put on the bottom at the center in the tightly closed chamber, and by pressing the actuator the contents were totally released. After two hours, the aluminum plates were taken out and the mortality of the house dust mites was counted after 3 days. The ratio of the number of the dead mites against the number of all the mites on the filter paper was calculated for the mortality. The results are shown in Table 1.

TABLE 1

| Tested aerosol | Mortality of mites (%) |
| --- | --- |
| Aerosol 1 | 84 |
| Aerosol 2 | 83 |
| Aerosol 3 | 85 |
| Aerosol 4 | 82 |
| Reference Aerosol 1 | 20 |
| Reference Aerosol 2 | 17 |
| Reference Aerosol 3 | 20 |
| Reference Aerosol 4 | 26 |

What is claimed is:

1. A method for controlling pests which comprises applying to pests or the locus where pests inhabit, a pesticidal liquid composition which comprises 2-methoxycarbonyl-4-chlorotrifluoromethanesulfonanilide, a propellant and a mixture of saturated $C_{13-17}$ hydrocarbons, wherein the amount of 2-methoxycarbonyl-4-chlorotrifluoromethanesulfonanilide is 0.01 to 5% by weight and the total amount of said saturated hydrocarbons is 35 to 99.9% by weight therein, and wherein the total of the pesticidal aerosol composition is applied.

2. A total-release pesticidal aerosol which comprises a pesticidal liquid composition which comprises 2-methoxycarbonyl-4-chlorotrifluoromethanesulfonanilide, a propellant and a mixture of saturated $C_{13-17}$ hydrocarbons, wherein the amount of 2-methoxycarbonyl-4-chlorotrifluoromethanesulfonanilide is 0.01 to 5% by weight and the total amount of said saturated hydrocarbons is 35 to 99.9% by weight therein, and wherein the aerosol is charged in a total-release aerosol container.

3. A total-release pesticidal aerosol which comprises a pesticidal liquid composition which comprises 2-methoxycarbonyl-4-chlorotrifluoromethanesulfonanilide, a propellant and a mixture of a mixture of saturated $C_{13-17}$ hydrocarbons, wherein the amount of 2-methoxycarbonyl-4-chlorotrifluoromethanesulfonanilide is 0.01 to 5% by weight, the total amount of said saturated hydrocarbons is 35 to 99.9% by weight therein, the amount of the pesticidal liquid composition is from 20 to 50% by weight and the amount of the propellant is from 50 to 80% in the pesticidal aerosol composition; and wherein the aerosol is charged in a total-release aerosol container.

* * * * *